United States Patent [19]
Lee et al.

[11] Patent Number: 5,929,091
[45] Date of Patent: Jul. 27, 1999

[54] METHOD OF LOWERING PLASMA LEVELS OF LIPOPROTEIN(A)

[75] Inventors: Helen Tsenwhei Lee; Randy Ranjee Ramharack, both of Ann Arbor, Mich.

[73] Assignee: Warner-Lambert Company, Morris Plains, N.J.

[21] Appl. No.: 09/166,678

[22] Filed: Oct. 5, 1998

Related U.S. Application Data

[60] Provisional application No. 60/067,252, Dec. 3, 1997.
[51] Int. Cl.⁶ .................................................. A61K 31/445
[52] U.S. Cl. ............................................................ 514/323
[58] Field of Search ................................................ 514/323

[56] References Cited

U.S. PATENT DOCUMENTS 5,595,872   1/1997   Wetterau, II et al. ........................ 435/6

*Primary Examiner*—Kimberly Jordan
*Attorney, Agent, or Firm*—Charles W. Ashbrook

[57] ABSTRACT

The present invention comprises a method of lowering plasma levels of Lp(a) in animals by administering an effective Lp(a)-reducing amount of a microsomal triglyceride transfer protein inhibitor of the structural formula:

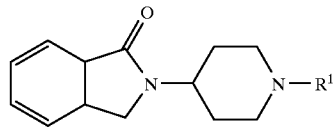

or a pharmaceutically acceptable salt thereof, wherein $R^1$ is alkyl, alkenyl alkynyl, aryl, heteroaryl, arylalkyl, heteroarylalkyl, cycloalkyl, or cycloalkylalkyl, each of which is independently optionally substituted through available carbon atoms with 1, 2, or 3 groups selected from halo, alkyl, alkenyl, alkoxy, aryloxy, aryl, arylalkyl, alkylmercapto, arylmercapto, cycloalkyl, cycloalkylalkyl, heteroaryl, and heteroarylalkyl. By lowering Lp(a) levels, the animals are protected against developing premature atherosclerosis and consequent cardiovascular and cerebrovascular diseases.

3 Claims, No Drawings

METHOD OF LOWERING PLASMA LEVELS OF LIPOPROTEIN(A)

This application claims the benefit of U.S. Provisional Application No. 60/067,252 filed Dec. 3, 1997.

BACKGROUND OF THE INVENTION

1. Field of the Invention

This invention relates to a method for lowering plasma levels of lipoprotein known as lipoprotein(a) (Lp(a)) in animals comprising administering a compound which inhibits microsomal triglyceride transfer protein.

2. Summary of the Related Art

Heart disease remains one of the leading causes of death. The high incidence of heart disease has led to the identification of various risk factors that may be controlled in an effort to reduce such disease. One risk factor is hypercholesterolemia which is a condition of high blood levels of cholesterol. Cholesterol is a fatty substance that is made by the liver and also is present in many foods. Cholesterol circulates in th blood and is associated with several forms of lipoproteins. One such lipoprotein is known as low-density lipoprotein (LDL). LDL associates with cholesterol from the liver to form LDL-cholesterol (LCL-C), which takes cholesterol from the liver to cells throughout the body. High levels of LDL-C have been shown to cause rapid clogging of coronary arteries with fatty deposits, resulting in atherosclerosis, which often leads to heart attacks. Levels of LDL-C can be reduced, for example, by modifying diet to reduce fat and cholesterol intake and by daily exercise. In contrast, a second form of lipoprotein, high density lipoprotein (HDL), associates with cholesterol to lower circulating levels of cholesterol by removing it from cells and recycling it to the liver for disposal.

A modified form of LDL is known as lipoprotein(a) (Lp(a)). Lp(a) consists of LDL covalently linked to apolipoprotein(a), (apo(a)) via a disulfide bond. Elevated levels of Lp(a) are associated with the development of atherosclerosis, coronary heart disease, myocardial infarction, cerebral infarction, and restenosis following balloon angioplasty. In fact, increased Lp(a) levels appear to be an excellent predictor for stroke. Accordingly, high concentrations of Lp(a) is one of the major risk factors leading to death from heart disease.

Wetterau et al. (U.S. Pat. No. 5,595,872) describe compounds that inhibit the protein known as microsomal triglyceride transfer protein (MTP) and have the structural formula:

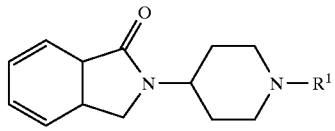

wherein $R^1$ is alkyl, alkenyl, alkynyl, aryl, heteroaryl, arylalkyl, heteroarylalkyl, cycloalkyl, or cycloalkylalkyl, each of which is optionally substituted through available carbon atoms with 1, 2, or 3 groups selected from halo, alkyl, alkenyl, alkoxy, aryloxy, aryl, arylalkyl, alkylmercapto, arylmercapto, cycloalkyl, cycloalkylalkyl, heteroaryl, and heteroarylalkyl. Examples of oxo-substituted groups are described in Cortizo, L., *J. Med. Chem.* 34: 2242–2247 (1991). In vitro, MTP catalyzes the transport of lipid molecules between phospholipid membranes. Wetterau & Zilversmit, *Chem, Phys. Lipids* 38, 205–22 (1985). The physiological role of MTP has not been demonstrated. Presumably, it plays a similar role in vivo, and thus plays some role in lipid metabolism. The subcellular (lumen of the microsomal fraction) and tissue distribution (liver and intstine) of MTP have led to speculation that it plays a role in the assembly of plasma lipoproteins, as these are the sites of plasma lipoprotein assembly. Wetterau & Zilversmit, *Biochem, Biophys. Acta*, 875: 610–7 (1986). Wetterau et al. determined that these MTP inhibiting compounds could decrease the MTP-catalyzed transfer of triglyceride (TG), cholesteryl ester (CE), and phosphatidylcholine (PC) between small unilamellar vesicles (SUV). Presently, however, there are no reports that the above reference compound are effective in decreasing the plasma levels of Lp(a). We have now discovered that plasma Lp(a) can be lowered by administering compounds of formula I, and accordingly an object of this invention is to provide a method for lowering Lp(a), and thereby treating and preventing coronary artery disease.

SUMMARY OF INVENTION

This invention provides a method for lowering plasma levels of Lp(a) in an animal (preferably a mammal) by administering an efficacious Lp(a)-lowering amount of a compound of the structural formula:

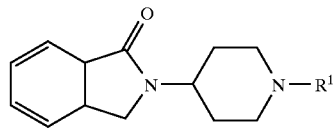

or a pharmnaceutically acceptable salt thereof, wherein $R^1$ is alkyl, alkenyl, alkynyl, aryl, heteroaryl, arylalkyl, heteroarylalkyl, cycloalkyl, or cycloalkylalkyl, each of which is independently optionally substituted through available carbon atoms with 1, 2, or 3 groups selected from halo, alkyl, alkenyl, alkoxy, aryloxy, aryl, arylalkyl, alkylmercapto, arylmercapto, cycloalkyl, cycloalkylalkyl, heteroaryl, and heteroarylalkyl. By lowering Lp(a) levels, the animals are protected against developing premature atherosclerosis and consequent coronary artery disease.

In particular, the present invention provides a method for lowering plasma levels of Lp(a) in an animal (preferably a mammal) by administering an efficacious Lp(a)-lowering amount of a compound of the formula:

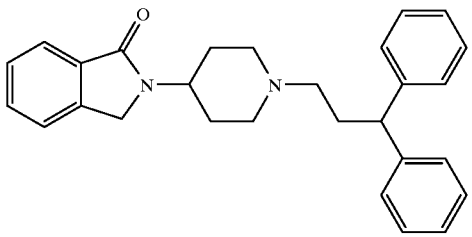

2-(1-(3,3-diphenylpropyl)-4-piperidyl)isoindolin-1-one or a pharmaceutically acceptable salt thereof.

The foregoing merely summarizes certain aspects of the present invention and is not intended, nor should be construed, as limiting the invention in any manner. All patents and publications cited herein establish the state of the art and are hereby incorporated by reference in their entirety.

DETAILED DESCRIPTION OF THE INVENTION

This invention provides a method for lowering plasma levels of Lp(a) in an animal (preferably a mammal) by administering an efficacious Lp(a)-lowering amount of a compound of the structural formula:

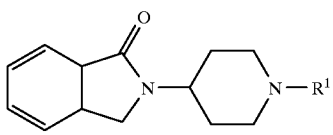

I or a pharmaceutically acceptable salt thereof, wherein $R^1$ is alkyl, alkenyl, alkynyl, aryl, heteroaryl, arylalkyl, heteroarylalkyl, cycloalkyl, or cycloalkylalkyl, each of which is independently optionally substituted through available carbon atoms with 1, 2, or 3 groups selected from halo, alkyl, alkenyl, alkoxy, aryloxy, aryl, arylalkyl, alkylmercapto, arylmercapto, cycloalkyl, cycloalkylalkyl, heteroaryl, and heteroarylalkyl. By lowering Lp(a) levels, the animals are protected against developing premature atherosclerosis and consequent cardiovascular and cerebrovascular diseases. All of the compounds to be utilized are either known or are readily prepared as described by Wetterau et al., U.S. Pat. No. 5,595,872 which is hereby expressly incorporated by reference.

As used herein, the terms "alkyl" and "alk," whether used alone or when used as a part of another group, mean a straight or branched chain hydrocarbyl groups having from 1 to 20 carbon atoms, with 1 to 12 preferred and 1 to 8 most preferred. Exemplary alkyl groups are methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof and the like.

The term "alkenyl" refers to both straight and branched chain hydrocarbyl groups of 1 to 20 carbon atoms, with 1 to 12 carbon atoms preferred and 1 to 8 most preferred, and having at least one double bond.

The term "alkynyl" refers to both straight and branched chain hydrocarbyl groups of 1 to 20 carbon atoms, with 1 to 12 carbon atoms preferred and 1 to 8 most preferred, and having at least one triple bond.

The term "cycloalkyl" means a saturated cyclic hydrocarbyl having from 3 to 20 and preferably 3–13 carbon atoms. Exemplary cycloalkyl groups include cyclopropyl, cyclobutyl, cyclopentyl, cyclohexyl, cycloheptyl, cyclooctyl, cyclodecyl, and cyclododecyl.

The terms "aryl" and "ar" mean a monocyclic or bicyclic aromatic group containing from 6 to 10 carbon atoms in the ring portion, such as phenyl or napthyl, and may be optionally substituted.

The term "heteroaryl" means a 5 or 6 membered aromatic ring having 1 or 2 heteroatoms (i.e., N, S, or O) that may be located at any position within the ring as well as such rings fused to an aryl (e.g., benzothiophenyl, indolyl). Exemplary heteroaryl groups include pyrrolyl, furanyl, thiophenyl, imidazolyl, oxazolyl, thiazolyl, pyrazolyl, pyridyl, pyrimidinyl, and the link, and may be optionally substituted and/or fused to an aryl such as indolyl and benzothiophenyl.

In a preferred embodiment, the present invention provides a method for lowering plasma levels of Lp(a) in an animal (preferably a mammal) by administering an efficacious amount of a compound II having the structural formula:

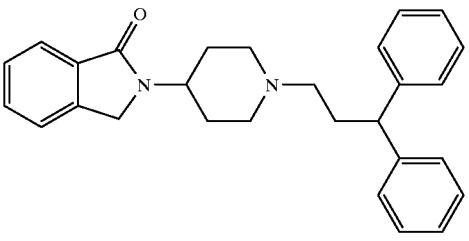

II 2-(1-(3,3-diphenylpropyl)-4-piperidyl)isoindolin-1-one or a pharmaceutically acceptable salt thereof. Particularly preferred is 2-(1-(3,3-diphenylpropyl)-4-piperidyl) isoindolin-1-one hydrochloride.

For use in the method of this invention, the compounds of formula I, or, preferably II, are preferably combined with one or more pharmaceutically acceptable diluents, carriers, excipients, or the like, for convenient oral, parenteral, and topical administration to animals, preferably humans. The compounds of formula I are ideally suited to formulation for oral administration in the form of tablets, capsules, dispersible powders, granules, suspensions, elixirs, buccal seals, and the like. The formulations typically will contain from about 1% to about 90% by weight of active compounds of formula I, and more commonly from about 5% to about 60% by weight.

Oral formulations can contain, for suspensions, from about 0.05% to about 5% by weight of a suspending agent, such as talc or the like, and syrups will contain from about 10% to about 50% by weight of a sugar such as dextrose. Tablets may contain normal amounts of binders, stabilizers, and common diluents such as corn starch and sugars. Parenteral formulations, for instance, solutions for IV injection, will be made by dissolving or suspending the compounds of formula I in a solvent such as isotonic saline or 5% glucose in sterile water.

The dose of compounds of formula I to be administered is that amount which is effective for lowering plasma levels of Lp(a) in an animal. Formulations utilizing one or more of the compounds if formula I are contemplated in the present invention.

The effective dosage of active ingredient employed may vary depending on the particular compound employed, the mode of administration, and the severity of the condition being treated. However, in general, satisfactory results are obtained when the compounds of formula I are administered at a daily dosage of from about 0.5 to about 500 mg/kg of animal body weight, preferably given in divided doses two to four times a day, or in sustained-release form. For most large mammals, such as humans, the total daily dosage is form about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The compounds of formula I may be administered orally as well as by intravenous, intramuscular, or subcutaneous routes. Solid carriers include starch, lactose, dicalcium phosphate, microcrystalline cellulose, sucrose, and kaolin, while liquid carriers include sterile water, polyethlene glycols, nonoinic surfactants, and edible oils such as corn, peanut, and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT, and BHA.

The preferred pharmaceutical compositions from the stand point of ease of preparation and administration are solid compositions, particularly tablets and hard-filled or liquid-filled capsules. Oral administration of the compounds of formula I is preferred.

These active compounds may also be administered parenterally or intraperitoneally Solutions or suspensions of these active compounds as a free base or pharmacologically acceptable salt can be prepared in water suitable mixed with a surfactant such as hydroxy-propylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powder for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing, for example, water, ethanol, polyol (eg, glycerol, propylene glycol, and liquid polyethylene glycol), suitable mixtures thereof, and vegetable oils.

Suitable cream, lotion, gel, stick, ointment, spray aerosol formulations that may be used for compounds of formula I and, preferably, II (or, if appropriate, a pharmaceutically acceptable salt thereof) are conventional formulations well known in the art, for example, as described in standard text books such as Harry's Cosmeticology published by Leonard Hill Books, Remington's Pharmaceutical Sciences. and the British and US Pharmacopoeias.

The compounds may also be encapsulated in liposomes to allow an intravenous administration of the drug. The liposomes suitable for use in the intention are lipid vesicles and may include plurilamellar lipid vesicles, small sonicated multimellar vesicles, reverse phase evaporation vesicles, large multilamellular vesicles, and the like, wherein the lipid vesicles are formed by one or more phospholipids such as phosphotidylcholine, phosphatidylglycerol, sphingomyelin, phospholactic acid, and the like. In addition, the liposomes may also comprise a sterol component such as cholesterol.

Some typical formulations which can be administered to humans are as follows:

Tablet Formulation 2-(1-(3,3-diphenylpropyl)-4-piperidyl)isoindolin-1-one hydrochloride (250 mg) is blended to uniformity with 100 mg of corn starch and 50 mg of lactose. The mixture is compressed into a tablet. Such tablets are administered orally at the rate of one to three times a day.

Preparation of Oral Suspension

| Ingredient | Amount |
|---|---|
| 2-(1-(3,3-diphenylpropyl)4-piperidyl)isoindolin-1-one hydrochloride | 500 mg |
| Sorbitol solution (70% NF) | 40 mL |
| Sodium benzoate | 150 mg |
| Saccharin | 10 mg |
| Red dye | 10 mg |
| Cherry flavor | 50 mg |
| Distilled water qs OD | 100 mL |

The sorbitol solution is added to 40 mL of distilled water and the retinoid is suspended thereon. The saccharin, sodium benzoate, flavor, and dye are added and dissolved. The volume is adjusted to 100 mL with distilled water. Each milliliter of syrup contains 5 mg of 2-(1-(3,3-diphenylpropyl)-4-piperidyl)isoindolin-1-one hydrochloride.

Suppositories

A mixture of 400 mg 2-(1-(3,3-diphenylpropyl)-4-piperidyl)isoindolin-1-one hydrochloride and 600 mg of theobroma oil is stirred at 60° C. to uniformity. The mixture is cooled and allowed to harden in a tapered mold to provide a 1-g suppository.

Parenteral Solution

In a solution of 700 mL of propylene glycol and 200 mL of sterile water is suspended 20.9 g of 2-(1-(3,3-diphenylpropyl)-4-piperidyl)isoindolin-1-one hydrochloride. The pH is adjusted to pH 6.5 with dilute sodium hydroxide, and the volume is made up to 100 mL with water for injection. The formulation is sterilized, filled into 5.0 mL ampoules each containing 2.0 mL (representing 40 mg of drug), and sealed under nitrogen.

Preferred formulations are those incorporating any of the preferred compounds of formula I to be utilized to lower Lp(a). Specifically preferred is 2-(1-(3,3-diphenylpropyl)-4-piperidyl)isoindolin-1-one hydrochloride.

Those skilled in the art will recognize that the compounds of formula I can be prepared according to the above teachings and examples below and combined with a wide variety of other chemicals for use in a composition that is effective in lowering plasma levels of Lp(a) in animals.

The following Example is provided for illustrative purposes only and is not intended, nor should it be construed, as limiting the invention in any manner. Those skilled in the art will appreciate that variations on and modifications of the following can be made without exceeding the spirit or scope of the invention.

EXAMPLE

Evaluation of 2-[1-3,3-diphenyl-2-propenyl)-4-piperidinyl-2,3-dihydro-1H-isoindol-1-one hydrochloride for Lowering Lp(a)

2-(1-(3,3-diphenylpropyl)-4-piperidyl)isoindolin-1-one hydro-chloride was evaluated for lowering Lp(a) levels in animals. This compounds was evaluated according to the following protocol.

HepG2 cells were obtained from the American Type Culture Collection (ATCC accession no. HB-8065) and permanently transfected with a human apo(a) cDNA containing 17-kringles. The 17-kringle apo(a) cDNA contained 24 nucleotides of 5'-untranslated sequence; leader sequence; kringle IV (KIV) type-1; eight copies of KIV type-2; KIV types 3–10; kringle V; protease domain; and 67 nuclcotides of 3'-untranslated region. The 17-kringle cDNA was cloned into the eukaryclitc expression vector pcDNA-Amp (In Vitrogen, Carlsbad, Calif.) that contains the cytomegalovius (CMV) immeidate early gene enhancer/propter and SV40 transcription termination and polyadenylation signals. This expression construct was co-transfected with pRc/CMV (In Vitrogen), which contains the neomycin resistance gene, into 50% confluent HepG2 cells using the calcium phosphate method (Madison, Wis.). Cells permanently transfected with the later constructs were selected by their ability to form colonies in the presence of the neomycin analogue G418. Selected colonies expressing Lp(a) as a result of the covalent association of recombinant apo(a) with edogenous apoB100-LDL were screened by ELISA as described below. Of these, the colony expressing the highest relative level of Lp(a) (K-17, 145.9) was used for all experiments.

Apo(a) cDNA transfected HepG2 cells (K-17, 145.9) were plated at a density of 75,000 cell/well using 96-well plates in Dulbecco's Modified Eagle Medium (DMEM), supplemented with 5.5 mM glucose, 6.4 mM L-glutamine, 1 mM sodium pyruvate, 19.5 nM pyridoxine hydrochloride, 20 mM [4-(2-hydroxyethyl)-1-piperazineethanesulfonic acid (HEPES), 10% heat-inactivated fetal bovine serum (FBS), 100 units penicillin and 100 μg streptomycin/ml. Cells were grown in a humidified incubator maintained at 37° C. and 5% $CO_2$'95% air. The next morning, fresh DMEM (without FBS) containing 2-(1-(3,3-diphenylpropyl)-4-piperidyl)isoindolin-1-one hydrochloride at various concentrations (0.03, 0.1, 0.3; 1.0; 3.0, 10.0, 30.0, and 74 μM) in 0.74% DMSO was added to the cells and incubated for 8 hours. The media was harvested from the wells, transferred to polypropylene 96-well plate, sealed with 96-well caps and frozen immediately at −80° C. until needed for analysis. The cells left in the original plate were digested by adding 100 μL of 0.5 N NaOH to each well, wrapped tightly in Saran Wrap and allowed to incubate at room temperature overnight.

Lp(a) was measured in the culture media using the Apo-Tek ELISA kit as previously described (Taddei-Peters W C, Butman B T, Jones G R, Venetta T M, Macomber P F, Ransom J H: Quantification of lipoprotein(a) particles containing various apolipoprotein(a) isofroms by a monoclonal anti-apo(a) capture antibody and a polyclonal anti-apolipoprotein B detection antibody sandwich enzyme immunoassay. Clin. Chem. 1993; 39:1382–1389). Briefly, samples were incubated for one hour at 37° C. in wells coated with a monoclonal antibody specific for the apo(a) moiety of Lp(a). Unbound material was washed away, then a polyclonal antibody that recognizes apoB and conjugated to horseradish peroxidase was added and the plates incubated for 1 hour at 37° C. After washing, the plates were then incubated with the chromogenic substrate, tetramethybenzidine and hydrogen peroxide. During the substrate incubation a blue color forms that turns yellow when 2N sulfuric acid was added to stop the reaction. The absorbance of each well was read in a Organon Teknika 96-well plate reader at a wavelength of 450 mn.

Total cellular protein determination was done using the DC Bio-Rad Assay (Bio-Rad Laboratories, Richmond Calif.). In this assay, protein reacts with an alkaline copper tartrate solution and Folin reagent. The reaction reaches 95% maximum in 15 minutes but the color is stable for 1 hour. An aliquot of 10 μL from each well was transferred to a polystyrene 96-well plate then 25 μL of the copper tartrate solution was added followed by 200 μL of the Folin reagent. The assay incubates at room temperature for 20 minutes before reading the absorbance in each well with the 96-well plate reader at a wavelength of 690 nm.

The data is presented in Table 1 and is expressed as percent inhibition at various concentrations relative to cells treated with vehicle only.

TABLE 1

| Concentration of 2-(1-(3,3-diphenylpropyl)-4-piperidyl)isoindolin-1-one hydrochloride (μM) | Percent Lowering of Lp(a) |
| --- | --- |
| 0.03 | 5.0 ± 1.3 |
| 0.10 | 3.9 ± 1.9 |
| 0.3 | 2.0 ± 0.6 |
| 1.0 | 34.3 ± 3.0 |
| 3.0 | 57.6 ± 1.6 |
| 10.0 | 71.7 ± 0.6 |
| 30.0 | 78.7 ± 0.3 |
| 74.0 | 84.8 ± 0.6 |

We claim:

1. A method of lowering plasma Lp(a) levels in an animal comprising administering an Lp(a)-lowering amount of a compound of the structural formula:

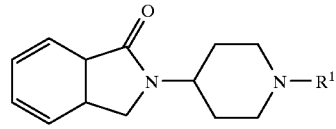

or a pharmaceutically acceptable salt thereof, wherein $R^1$ is alkyl, alkenyl, alkynyl, aryl, heteroaryl, arylalkyl, heteroarylalkyl, cycloalkyl, cycloalkylalkyl, each of which is independently optionally substituted through available carbon atoms with 1, 2, or 3 groups selected from halo, alkyl, alkenyl, alkoxy, aryloxy, aryl, arylalkyl, alkylmercapto, arylmercapto, cycloalkyl, cycloalkylalkyl, heteroaryl, and heteroarylalkyl.

2. The method of claim 1, wherein the compound is 2-(1-(3,3-diphenylpropyl)-4-piperidyl)isoindolin-1-one or a pharmaceutically acceptable salt thereof.

3. The method of claim 1, wherein the compound is 2-(1-(3,3-diphenylpropyl)-4-piperidyl)isoindolin-1-one hydrochloride.

* * * * *